(12) United States Patent  
Dehmeshki et al.

(10) Patent No.: US 7,133,546 B2
(45) Date of Patent: Nov. 7, 2006

(54) DIGITAL MEDICAL IMAGE ANALYSIS

(75) Inventors: Jamshid Dehmeshki, London (GB); Susan Alyson Wood, Mountain View, CA (US); Paul Richard Blelock Samuel, London (GB)

(73) Assignee: Medicsight PLC, London (GB)

( * ) Notice: Subject to any disclaimer, the term of this patent is extended or adjusted under 35 U.S.C. 154(b) by 2 days.

(21) Appl. No.: 11/138,956

(22) Filed: May 27, 2005

(65) Prior Publication Data

US 2006/0115135 A1    Jun. 1, 2006

(30) Foreign Application Priority Data

Nov. 29, 2004   (GB)   ................................. 0426177.2

(51) Int. Cl.
*G06K 9/00* (2006.01)
(52) U.S. Cl. ...................... 382/128; 382/129; 382/132; 382/133
(58) Field of Classification Search ................ 382/128, 382/129, 130, 131, 132, 133, 134; 708/203; 600/407; 128/920, 922; 607/28, 17; 705/2, 705/37
See application file for complete search history.

(56) References Cited

U.S. PATENT DOCUMENTS

| | | | | |
|---|---|---|---|---|
| 5,235,510 | A | | 8/1993 | Yamada et al. .............. 600/300 |
| 5,843,137 | A | * | 12/1998 | Condie et al. ................. 607/28 |
| 5,878,746 | A | | 3/1999 | Lemelson et al. ........... 600/407 |
| 5,902,325 | A | * | 5/1999 | Condie et al. ................. 607/28 |
| 5,983,251 | A | * | 11/1999 | Martens et al. .............. 708/203 |
| 6,058,322 | A | | 5/2000 | Nishikawa et al. .......... 600/408 |
| 6,430,430 | B1 | * | 8/2002 | Gosche ......................... 600/410 |
| 2002/0057850 | A1 | | 5/2002 | Sirohey et al. .............. 382/299 |
| 2004/0122790 | A1 | | 6/2004 | Walker et al. .................. 707/1 |

FOREIGN PATENT DOCUMENTS

EP    1398722 A2    3/2004

OTHER PUBLICATIONS

Agatston, Arthur A., et al., "Quantification of Coronary Artery Calcium Using Ultrafast Computed Tomography," *Journal of the American College of Cardiology*, vol. 15, No. 4, pp. 827-832 (Mar. 15, 1990).
ANALYZE ™ 7.5 File Format, 11 pages, available on Nov. 19, 2004 at http://www.mayo.edu/bir/PDF/ANALYZE75.pdf.
*Digital Imaging and Communication in Medicine (DICOM) Part 1: Introduction and Overview*, 21 pages, National Electrical Manufacturers Association, available on Nov. 19, 2004 as 03v04_01.pdf at ftp://medical.nema.org/medical/dicom/2004/03v04dif/ (Copyright 2004).

(Continued)

*Primary Examiner*—Anh Hong Do
(74) *Attorney, Agent, or Firm*—Sterne Kessler Goldstein & Fox, PLLC (57) ABSTRACT

A medical image is analyzed using an algorithm requiring input parameters. Values of the input parameters are derived from metadata, indicating properties of the medical image. For example, the metadata may indicate the type of image acquisition device or settings used to create the medical image. In another example, the metadata may relate to the patient upon whom the image is based. This allows optimum values to be selected for the parameters.

29 Claims, 8 Drawing Sheets
(1 of 8 Drawing Sheet(s) Filed in Color)

OTHER PUBLICATIONS

*Digital Imaging and Communication in Medicine* (*DICOM*) *Part 2: Conformance*, 287 pages, National Electrical Manufacturers Association, available on Nov. 19, 2004 as 03v04_02.pdf at ftp://medical.nema.org/medical/dicom/2004/03v04dif/ (Copyright 2004).

*Digital Imaging and Communication in Medicine* (*DICOM*) *Part 3: Information Object Definitions*, 970 pages, National Electrical Manufacturers Association, available on Nov. 19, 2004 as 03v04_03_02.pdf at ftp://medical.nema.org/medical/dicom/2004/03v04dif/ (Copyright 2004).

*Digital Imaging and Communication in Medicine* (*DICOM*) *Part 4: Service Class Specifications*, 359 pages, National Electrical Manufacturers Association, available on Nov. 19, 2004 as 03v04_04.pdf at ftp://medical.nema.org/medical/dicom/2004/03v04dif/ (Copyright 2004).

*Digital Imaging and Communication in Medicine* (*DICOM*) *Part 5: Data Structures and Encoding*, 106 pages, National Electrical Manufacturers Association, available on Nov. 19, 2004 as 03v04_05.pdf at ftp://medical.nema.org/medical/dicom/2004/03v04dif/ (Copyright 2004).

*Digital Imaging and Communication in Medicine* (*DICOM*) *Part 6: Data Dictionary*, 95 pages, National Electrical Manufacturers Association, available on Nov. 19, 2004 as 03v04_06.pdf at ftp://medical.nema.org/medical/dicom/2004/03v04dif/ (Copyright 2004).

*Digital Imaging and Communication in Medicine* (*DICOM*) *Part 7: Message Exchange*, 118 pages, National Electrical Manufacturers Association, available on Nov. 19, 2004 as 03v04_07.pdf at ftp://medical.nema.org/medical/dicom/2004/03v04dif/ (Copyright 2004).

*Digital Imaging and Communication in Medicine* (*DICOM*) *Part 8: Network Communication Support for Message Exchange*, 56 pages, National Electrical Manufacturers Association, available on Nov. 19, 2004 as 03v04_08.pdf at ftp://medical.nema.org/medical/dicom/2004/03v04dif/ (Copyright 2004).

*Digital Imaging and Communication in Medicine* (*DICOM*) *Part 10: Media Storage and File Format for Media Interchange*, 33 pages, National Electrical Manufacturers Association, available on Nov. 19, 2004 as 03v04_10.pdf at ftp://medical.nema.org/medical/dicom/2004/03v04dif/ (Copyright 2004).

*Digital Imaging and Communication in Medicine* (*DICOM*) *Part 11: Media Storage Application Profiles*, 76 pages, National Electrical Manufacturers Association, available on Nov. 19, 2004 as 03v04_11.pdf at ftp://medical.nema.org/medical/dicom/2004/03v04dif/ (Copyright 2004).

*Digital Imaging and Communication in Medicine* (*DICOM*) *Part 12: Media Formats and Physical Media for Media Interchange*, 54 pages, National Electrical Manufacturers Association, available on Nov. 19, 2004 as 03v04_12.pdf at ftp://medical.nema.org/medical/dicom/2004/03v04dif/ (Copyright 2004).

*Digital Imaging and Communication in Medicine* (*DICOM*) *Part 14: Grayscale Standard Display Function*, 55 pages, National Electrical Manufacturers Association, available on Nov. 19, 2004 as 03v04_14.pdf at ftp://medical.nema.org/medical/dicom/2004/03v04dif/ (Copyright 2004).

*Digital Imaging and Communication in Medicine* (*DICOM*) *Part 15: Security and System Management Profiles*, 75 pages, National Electrical Manufacturers Association, available on Nov. 19, 2004 as 03v04_15.pdf at ftp://medical.nema.org/medical/dicom/2004/03v04dif/ (Copyright 2004).

*Digital Imaging and Communication in Medicine* (*DICOM*) *Part 16: Content Mapping Resource*, 667 pages, National Electrical Manufacturers Association, available on Nov. 19, 2004 as 03v04_16.pdf at ftp://medical.nema.org/medical/dicom/2004/03v04dif/ (Copyright 2004).

European Search Report, issued in Appl. No. EP05252010.3, dated Nov. 17, 2005, (4 pages).

* cited by examiner

DIGITAL MEDICAL IMAGE ANALYSIS

RELATED APPLICATIONS

This application claims the benefit of the filing date of GB patent Application No. 0426177.2, filed Nov. 29, 2004, and EP patent Application No. EP05252010.3, filed Mar. 31, 2005, both of which are incorporated herein by reference in their entireties.

BACKGROUND OF THE INVENTION

1. Field of the Invention

The present invention relates to digital medical image analysis, particularly by means of a computer-implemented algorithm.

2. Background

Medical images are a valuable tool for detection, diagnosis and evaluation of response to treatment of disease, as well as surgical planning. A variety of physical techniques or modalities have been developed for producing these images, including projection X-rays, computed tomography (CT), ultrasound (US), positron emission tomography (PET) and magnetic resonance imaging (MRI). The images may be generated digitally (using, e.g., US, CT or MRI) or digitized from an analog image (e.g., film). Conventionally, trained radiologists or other clinicians review these images to facilitate detection of an abnormality, for example. A radiologist or clinician can review and annotate the digitized images and generate a report based on the review. All of the resultant data may be stored for later retrieval and analysis.

The task of a user (e.g., radiologist, clinician, etc.) can be made easier by reviewing the images with application software providing visualization and analysis tools to manipulate and evaluate these images in 2, 3 and 4 dimensions (for images that vary in time). However, the evaluation process can result in missed abnormalities because of normal limitations in human perception. This perception issue is worsened by the ever-increasing amount of information now available to the radiologist or clinician for review. Now, in the information-intense but resource- and time-constrained environments in which radiologists work, they are forced to make expedited decisions, potentially resulting in increased miss rate.

Computer Assisted Detection or Diagnosis (CAD) software has been designed to reduce errors of human perception, as well as to enhance the productivity of radiologists or other clinicians in an information-intense environment, by automatically performing for the user the more mundane tasks (e.g., automatic measurement) and focusing the radiologist's limited time on interpretation. CAD software can automatically or semi-automatically detect and measure abnormalities, characterize abnormalities, measure temporal progression or regression of disease and surgically plan based on CAD information. For example, the applicant's MedicHeart™, MedicLung™ and MedicColon™ diagnostic software perform semiautomatic and automatic analysis of CT scans of the heart, lung and colon, respectively.

CAD software uses algorithms to analyze a given medical image. No one algorithm is robust enough to analyze accurately all types of medical images. For example, abnormal structures in the lung have different image characteristics from those in the colon. Images acquired using different modalities or combinations of modalities (e.g., MRI, CT, US) have different resolutions and image characteristics, and hence require more specific algorithms to analyze them. Given a choice of CAD algorithms designed to more closely address the needs of a specific disease state or acquisition modality, the user of CAD software would likely opt for that algorithm designed more specifically (e.g., the clinical condition, modality or focused anatomy of the dataset) and select the appropriate algorithm for analysis of that type of image. Alternatively, the user may only be interested in analyzing one type of image and therefore only use one type of algorithm.

U.S. Pat. No. 5,235,510 to Yamada et al. describes a system for automating the selection of an appropriate algorithm for the analysis of a medical image by inspecting attribute data, identifying the image type and selecting an algorithm appropriate for that type.

Many CAD algorithms rely on a predefined set of parameter values for detection. For example, the Agatston method, as originally described in "Quantification of Coronary Artery Calcium Using Ultrafast Computed Tomography", Agatston A S, Janowitz W R, Hildner F J et al., J Am Coll Cardiol 1990 15: 827–832 (hereinafter "the Agatston article"), applies a threshold of 130 Hounsfield units (HU) to the CT image, and identifies all pixels above that threshold as containing calcium. A scoring system is then used to rate the severity of the calcification, based on the number of pixels above the threshold multiplied by a weight based on the highest intensity within the calcification. If the highest intensity is between 130 and 200 HU, then the weight is 1. If the highest intensity is between 200 and 300 HU, the weight is 2. If the highest intensity is greater than 300 RU, the weight is 3. The threshold of 130 HU works reasonably well with the types of CT scan images available at the time of publication of the Agatston article, but there is no general agreement as to how this threshold should be modified for new types of CT scan, such as data acquired with thinner collimation.

Alternatively, the CAD application software may allow the user to set the values of parameters used in the analysis. For example, CAR® software (available from Medicsight PLC, a company located in London, England), aspects of which are described in a prior patent application GB0420147.1 to Dehmeshki, provides a user interface allowing the user to interactively modify the parameters used by an algorithm. The results of any selected parameters are available to the user. While this user interaction provides great flexibility, the optimum parameter values may not be known. For example, the user may select a less optimal parameter value for analysis. In another example, the user may select the parameter value by trial and error, further impacting productivity.

Using predefined parameter values has the advantage of simplicity and consistency, but may not always provide better results, as compared to using parameter values that are not predefined. While user-defined parameter values provide greater flexibility, they may not provide better results unless the optimum parameter values are chosen. Allowing the user to set parameter values adds to the complexity of CAD software.

U.S. Pat. No. 6,058,322 describes an interactive user modification function in which the software displays detected microcalcifications, and the user may then add or delete microcalcifications. The software modifies its estimated likelihood of malignancy accordingly.

EP-A-1398722 describes a "dynamic CAD" system in which an image is processed to identify features of interest and to extract parameters from the features of interest. The image is post-processed using the extracted parameters to generate a second image. The post-processing parameters are derived from the image itself, rather than from metadata associated with the image.

U.S. Pat. No. 5,878,746 describes a computerized diagnostic system, which may process medical images to derive feature vectors. The system inputs the feature vectors together with other clinical parameters into a "fact database", which is then processed to obtain a diagnosis.

BRIEF SUMMARY OF THE INVENTION

According to one aspect of the invention, there is provided a method of analyzing a digital medical image using a computer-implemented algorithm having one or more variable parameters, wherein the value of at least one of the parameters is selected automatically according to at least one indicated attribute associated with, but not derived from, the medical image.

At least one of the parameters may be selected according to at least one indicated attribute of the patient upon whom the image is based. At least one of the attributes may be a suspected or diagnosed clinical indication of the patient. At least one of the attributes may be all or a component of the clinical history of the patient. At least one of the attributes may be non-clinical patient data, such as age, sex, height, weight or other statistical data.

At least one of the parameters may be selected according to an indicated property or setting of an image acquisition device used to prepare the image. The property may be the type (e.g., make and/or model) of the acquisition device. The property value or setting may be a resolution, dose or other setting specific to the particular acquisition protocol used to create the image.

At least one attribute may be indicated by metadata associated with the image. For example, the indicated attribute may be in a header field of a file containing the medical image, a tag associated with the image, or data linked to the image. The metadata may be read automatically and used to set parameter values for the algorithm, without user intervention.

The at least one attribute may be indicated by the user, without requiring the user to specify parameter values used by the algorithm. For example, the user may input the clinical indication, clinical history data, or non-clinical statistical data for the patient. The method then selects the at least one parameter value according to the at least one attribute indicated by the user.

In one embodiment, the automated method selects an optimum parameter value set, which is then provided as input to the algorithm. The image is processed using the algorithm based on the selected one or more parameter values. A plurality of optimum parameter value sets may be stored, and the optimum parameter value set may be selected from the stored plurality of sets. Additionally or alternatively, the optimum parameter value set may be derived by a predetermined function of at least the one or more indicated attributes. The optimum parameter value sets and their relationship to the indicated attributes may be derived theoretically or empirically.

According to a further aspect of the invention, the relationship between attribute values and optimum parameter values is derived from a plurality of training digital medical images, each having associated metadata, for which analysis results are available.

In one embodiment, training images having known corresponding attributes are analyzed using the algorithm. Preferably, many training images are analyzed. The training images may be images of real patients or of phantoms (i.e., objects simulating structures in the body, and having known attributes). The analysis may be controlled by one or more users who are able to select the parameter values for the algorithm manually (for example, using the CAR® software described above). Preferably, the users are experienced radiologists and/or experienced users of the algorithm. The training images may also be inspected visually by experienced radiologists to facilitate determining abnormalities in the training images. The optimum parameter values for each training image may be determined as the parameter values for which the results of the algorithm most closely match the results of the visual inspection and/or as the optimum parameter values chosen by the experienced users. A plurality of different optimum parameter value sets may be derived for each training image, as a function of the desired sensitivity or specificity.

For example, the training images may be selected from images stored locally. In another example, the training images may be available over a local or wide-area network. A search may be performed to identify suitable training images. Selected training images may be weighted according to their relevance to the candidate image.

A relationship is then derived between the optimum parameter value sets for each of the training images and the associated attributes of the training images. The relationship may comprise a function, one or more rules, a neural net and/or fuzzy logic, to provide some examples.

An advantage of the method is that, for a given algorithm, the optimum parameters for that algorithm may be selected for any image. The optimum parameters may be selected automatically, without requiring user intervention, thus alleviating the time constraints on the radiologist. This may also enable accurate batch analysis of multiple images. In the case of the attributes being indicated by the user, this allows the user to enter known and/or meaningful data, rather than requiring the user to choose parameters that may have little meaning outside the context of the algorithm. However, the user may specify the criteria for which optimum parameters are selected, such as greater sensitivity or specificity.

The image metadata may have been entered by an operator of the image acquisition device or by a technician subsequent to the capture of the image. Alternatively, the image metadata may have been recorded automatically by the image acquisition device and/or its associated control devices. Hence, a user who enters the attributes and a user to whom the results of the algorithm are presented need not necessarily be the same. The entry of attributes and the review of the results may be performed using respective distinct data entry and output devices.

The derived optimum parameter values may be set as default parameter values, which the user may modify by means of user manipulated filters. The results of using the modified parameter values to analyze the image may be displayed prior to output of the final results. The results may be a modified version of the image, displayed so as to allow comparison with the original image. This allows the result of the user's visual inspection of the original image to be compared to the result of the analysis using the algorithm. According to an embodiment, the digital medical image and the modified version of the image are displayed simultaneously. In another embodiment, the digital medical image and the modified version of the image are displayed alternately.

The method of the present invention may be performed by software, hardware, firmware or any combination thereof.

BRIEF DESCRIPTION OF THE DRAWINGS/FIGURES

The patent or application file contains at least one drawing executed in color. Copies of this patent or patent application publication with color drawing(s) will be provided by the Office upon request and payment of the necessary fee.

The accompanying drawings, which are incorporated herein and form part of the specification, illustrate embodiments of the present invention and, together with the description, further serve to explain the principles of the invention and to enable a person skilled in the pertinent art(s) to make and use the invention. In the drawings, like reference numbers indicate identical or functionally similar elements. Additionally, the leftmost digit(s) of a reference number identifies the drawing in which the reference number first appears.

DETAILED DESCRIPTION OF THE EMBODIMENTS

I. Digital Medical Image

The present invention is applicable to digital medical images. One example of such an image is a CT scan image. A CT scan image is a digital image comprising one or a series of CT image slices obtained from a CT scan of an area of a human or animal patient. Each slice is a 2-dimensional digital grey-scale image of the x-ray absorption of the scanned area. The properties of the slice depend on the CT scanner used. For example, a high-resolution multi-slice CT scanner may produce images with a resolution of 0.5–0.6 mm/pixel in x and y directions (i.e., in the plane of the slice). Each pixel may have 32-bit grayscale resolution. The intensity value of each pixel is normally expressed in Hounsfield units (HU). Sequential slices may be separated by a constant distance along a z direction (i.e., the scan separation axis). For example, the sequential slices may be separated by a distance in a range of approximately 0.75–2.5 millimeters (mm). According to an embodiment, the scan image is a three-dimensional (3D) grey scale image, for example, with an overall size that depends on the area and/or number of slices scanned. In another embodiment, the scan image is a single two-dimensional (2D) grayscale image representing a single slice.

The CT scan may be obtained by any CT scanning technique, such as electron beam computed tomography (EBCT), multi-detector or spiral scan or any technique which produces as output a 2D, 3D or 4D image representing X-ray absorption.

The invention is not limited to CT scan images, and may be applied to other digital medical images, such as MRI, US, PET or projection X-ray images. Conventional X-ray images may be developed on an X-ray film prior to being digitized.

Figure 1:
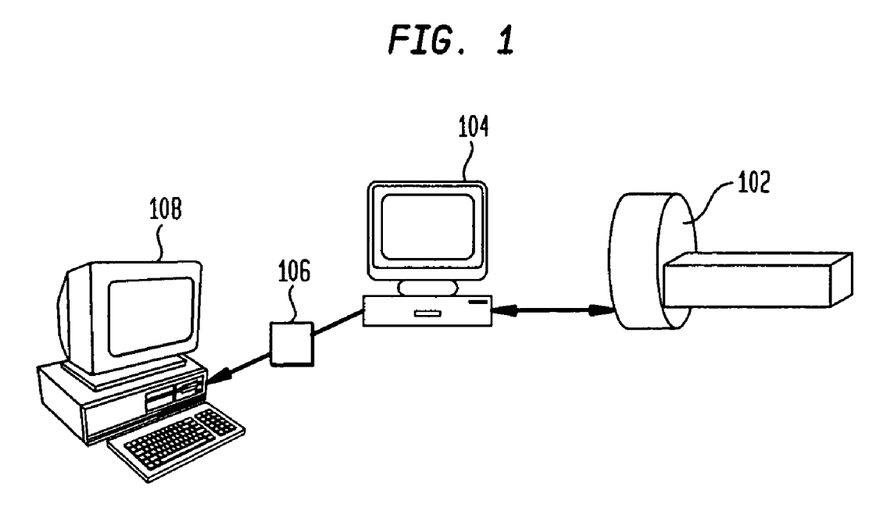
FIG. 1 is a schematic diagram showing a medical image acquisition device and a remote computer to process image data received from the medical image acquisition device according to an embodiment of the present invention.

As shown in FIG. 1, the scan image is created by a computer 104. Computer 104 receives scan data from a scanner 102 and constructs the scan image based on the scan data. The scan image is often saved as an electronic file or a series of files which are stored on a storage medium 106, such as a fixed or removable disc. The file or files include metadata associated with the scan image. The scan image may be processed by computer 104, or the scan image may be transferred to another computer 108 which runs software for processing and displaying the image as described below. The image processing software may be stored on a computer recordable medium, such as a removable disc, or downloaded over a network.

II. Example Computer System

Computer 104 or 108 can be any type of computer system, including but not limited to an example computer system 200 described below with reference to FIG. 2. Embodiments of the present invention may be implemented as programmable code for execution by computer system 200. Various embodiments of the invention are described in terms of computer system 200. After reading this description, it will become apparent to a person skilled in the art how to implement the invention using other computer systems and/or computer architectures.

Figure 2:
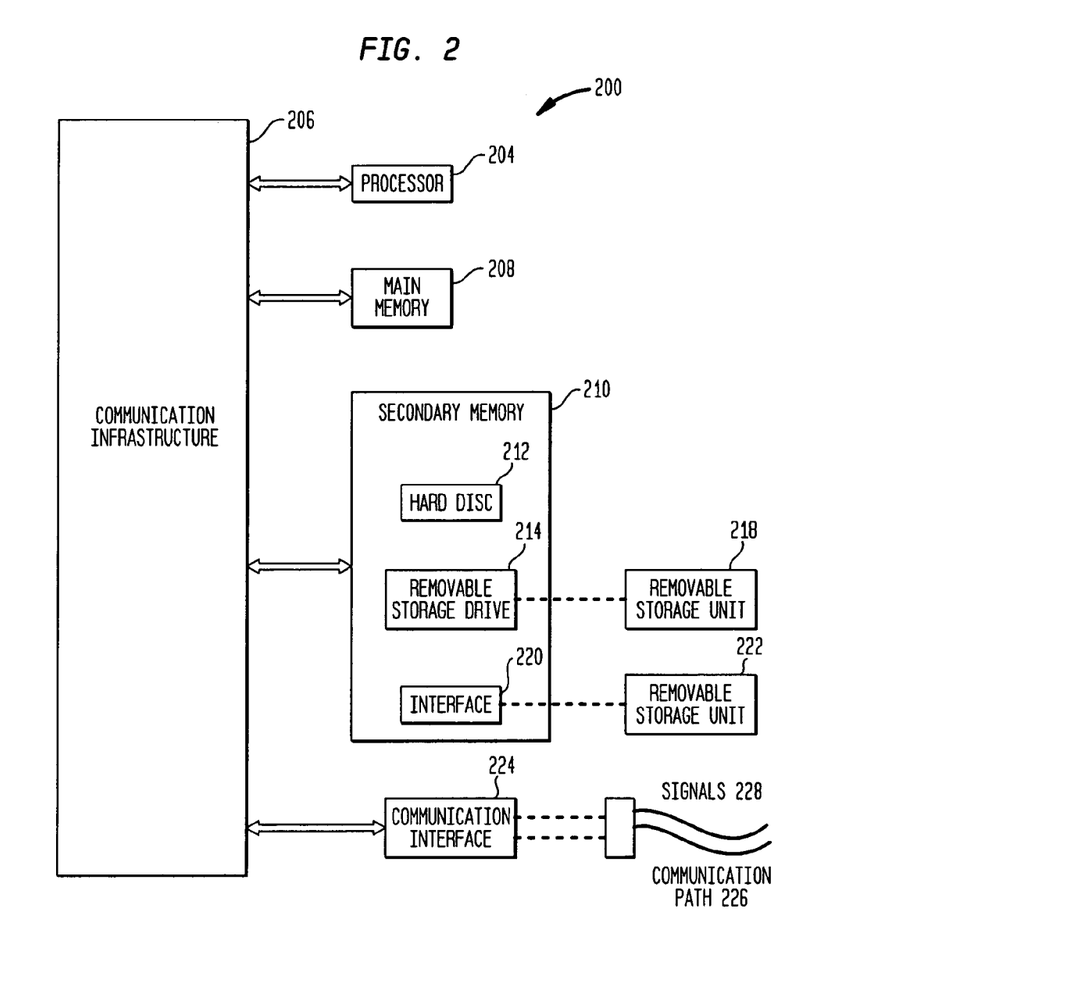
FIG. 2 is a block diagram of an example computer system, in which the present invention may be implemented as programmable code.

Referring to FIG. 2, computer system 200 includes one or more processors, such as processor 204. Processor 204 may be any type of processor, including but not limited to a special purpose or a general-purpose digital signal processor. Processor 204 is connected to a communication infrastructure 206 (for example, a bus or network).

Computer system 200 also includes a main memory 208, preferably random access memory (RAM), and may also include a secondary memory 210. Secondary memory 210 may include, for example, a hard disk drive 212 and/or a removable storage drive 214, representing a floppy disk drive, a magnetic tape drive, an optical disk drive, etc. Removable storage drive 214 reads from and/or writes to a removable storage unit 218 in a well-known manner. Removable storage unit 218 represents a floppy disk, magnetic tape, optical disk, etc., which is read by and written to by removable storage drive 214. As will be appreciated, removable storage unit 218 includes a computer usable storage medium having stored therein computer software and/or data.

In alternative implementations, secondary memory 210 may include other similar means for allowing computer programs or other instructions to be loaded into computer system 200. Such means may include, for example, a removable storage unit 222 and an interface 220. Examples of such means may include a program cartridge and cartridge interface (such as that found in video game devices), a removable memory chip (such as an EPROM or a PROM) and associated socket, and other removable storage units 222 and interfaces 220 which allow software and data to be transferred from removable storage unit 222 to computer system 200.

Computer system 200 may also include a communication interface 224. Communication interface 224 allows software and data to be transferred between computer system 200 and external devices. Examples of communication interface 224 may include a modem, a network interface (such as an Ethernet card), a communication port, a Personal Computer Memory Card International Association (PCMCIA) slot and card, etc. Software and data transferred via communication interface 224 are in the form of signals 228, which may be electronic, electromagnetic, optical, or other signals capable of being received by communication interface 224. These signals 228 are provided to communication interface 224 via a communication path 226. Communication path 226 carries signals 228 and may be implemented using wire or cable, fiber optics, a phone line, a cellular phone link, a radio frequency link, or any other suitable communication channel. For instance, communication path 226 may be implemented using a combination of channels.

In this document, the terms "computer program medium" and "computer usable medium" are used generally to refer to media such as removable storage unit 218, a hard disk installed in hard disk drive 212, and signals 228. These computer program products are means for providing software to computer system 200.

Computer programs (also called computer control logic) are stored in main memory 208 and/or secondary memory 210. Computer programs may also be received via communication interface 224. Such computer programs, when executed, enable computer system 200 to implement the present invention as discussed herein. Accordingly, such computer programs represent controllers of computer system 200. Where the invention is implemented using software, the software may be stored in a computer program product and loaded into computer system 200 using removable storage drive 214, hard disk drive 212, or communication interface 224, to provide some examples.

In alternative embodiments, the invention can be implemented as control logic in hardware, firmware, or software or any combination thereof.

III. General Method

According to an embodiment of the present invention, a method is provided to process a digital medical image using an algorithm to identify one or more medical abnormalities. In an embodiment, the method is performed using a computer program, though the scope of the invention is not limited in this respect.

Figure 3:
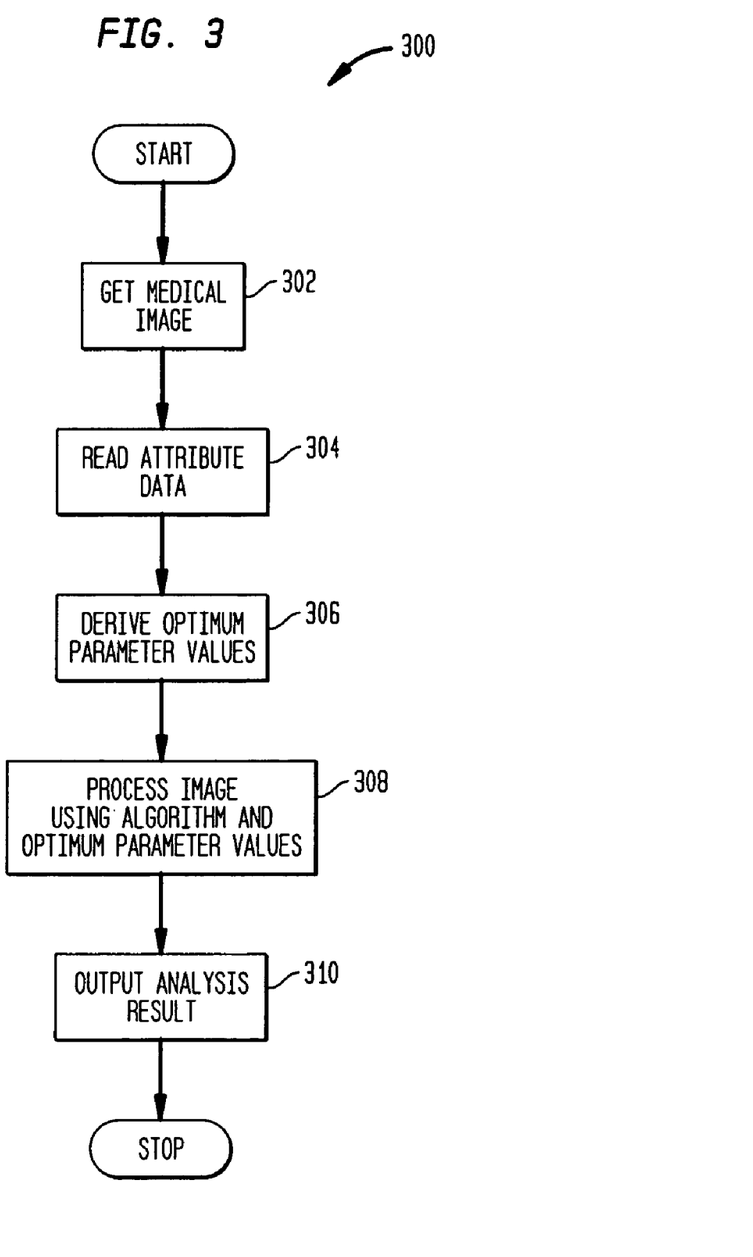
FIG. 3 is a flowchart of the main steps of a method according to an embodiment of the present invention.

FIG. 3 is a flowchart 300 of the main steps (steps 302–310) of the method according to an embodiment of the present invention. The invention, however, is not limited to the description provided by the flowchart 300. Rather, it will be apparent to persons skilled in the relevant art(s) from the teachings provided herein that other functional flows are within the scope and spirit of the present invention. Flowchart 300 will be described with continued reference to the data relationships illustrated in FIG. 4, though the method is not limited to that embodiment.

Figure 4:
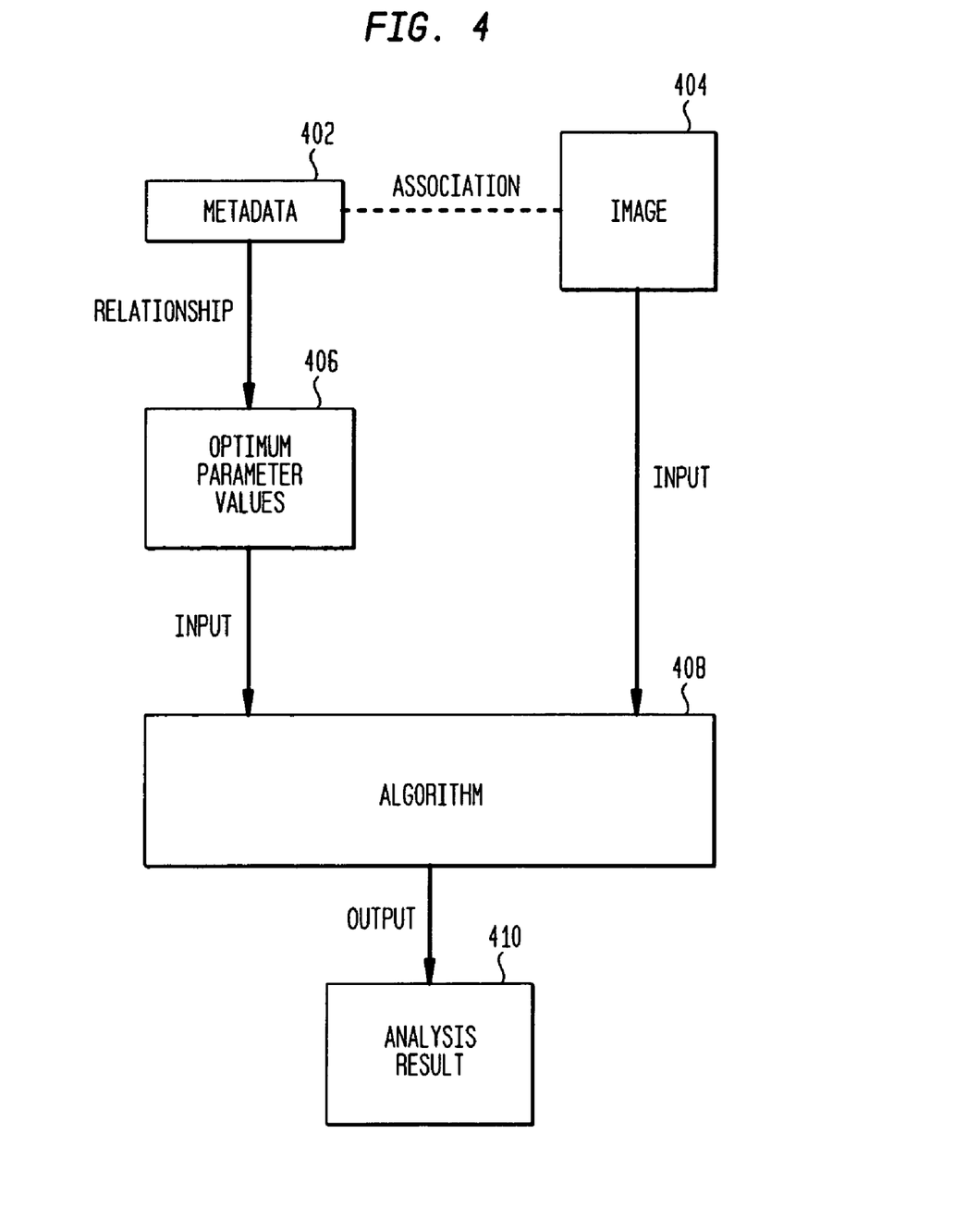
FIG. 4 is a diagram of data relationships corresponding to the method according to an embodiment of the present invention.

FIG. 4 is a diagram of data relationships corresponding to the method according to an embodiment of the present invention. In FIG. 4, the metadata 402 is associated with the medical image 404. The optimum parameter values 406 are based on the metadata 402. As shown in FIG. 4, the medical image 404 and the optimum parameter values 406 are provided as inputs to the algorithm 408, which provides the analysis result 410 as an output.

Referring now to FIG. 3, a medical image 404 is accessed at step 302. Metadata 402 associated with the medical image 404 is accessed at step 304. At step 306, optimum parameter values 406 are derived from the metadata 402. According to an embodiment, the optimum parameter values 406 are derived using a predetermined relationship between values of the metadata 402 and the optimum parameter values 406. For example, the relationship between the optimum parameter values 406 and the metadata 402 can be determined, such that the optimum parameters 406 may be derived thereafter based on the metadata 402 and the relationship. At step 308, the medical image 404 is processed using an algorithm 408 and the optimum parameter values 406. For instance, the medical image 404 and the optimum parameter values 406 may be provided to the algorithm 408, which produces an analysis result 410 at step 310, based on the medical image 404 and the optimum parameter values 406. Each of the steps 302–310 mentioned above is described in detail below with reference to FIG. 4.

IV. Image Metadata

Referring to steps 302 and 304, the metadata 402 may be generated at substantially the same time as the medical image 404 is created, for example by the computer 104 and/or the scanner 102. The metadata 402 may be created automatically and/or entered by a user of the computer 104.

As an example of automatically created data, a constant attribute of the scanner 102, such as its modality, make and/or model may be recorded as the metadata 402 for each image 404. As another alternative or additional example, a variable attribute specific to each image 404, such as a setting for the scan used to create that image 404, may be recorded as the metadata 402. The setting may be an image resolution, a contrast setting, a radiation intensity setting or any other setting appropriate to the modality and/or type of the scanner 102.

As an example of user-entered data, the user of the computer 104 may enter one or more attributes of the patient scanned by the scanner 102 to create the image 404. The attributes may include one or more of: clinical information about the patient, such as a diagnosed clinical indication; a clinical estimation, such as a suspected clinical indication; and patient statistics, such as age, sex, height, weight or other statistical data which is not in itself a clinical indication.

The metadata 402 may be stored in a header field of a file containing the digital medical image 404, in a tag associated with the image 404, and/or in data linked to the image 404. For example, the metadata 402 and digital medical image 404 may be recorded in the Digital Imaging and Communications in Medicine (DICOM) format, which stores metadata in a header of an image file, as defined by the specification available on 19 Nov. 2004 at: ftp://medical.nema.org/medical/dicom/2004/03v04dif/.

Alternatively, the metadata 402 and digital medical image 404 may be recorded in the Analyze format, which stores metadata in a separate file from the image, as defined by the specification available on the same date at: http://www.mayo.edu/bir/PDF/ANALYZE75.pdf.

In step 306, optimum parameter values 406 are derived. Examples of such optimum parameter value derivation methods are described further below.

V. Algorithm

Referring to steps 308 and 310, the algorithm 408 takes as its input the medical image 404 and one or more optimum parameter values 406. Based on at least these inputs, the algorithm analyzes the image 404 to generate an analysis result 410 indicative of any abnormality in the object of the image 404. For example, the analysis result 410 may indicate one or more of: whether an abnormality is present; the position of one or more abnormalities; a confidence level of the detection of an abnormality; a type of an abnormality; and a quantity relating to an abnormality, such as a mass or a volume.

Figure 5A:
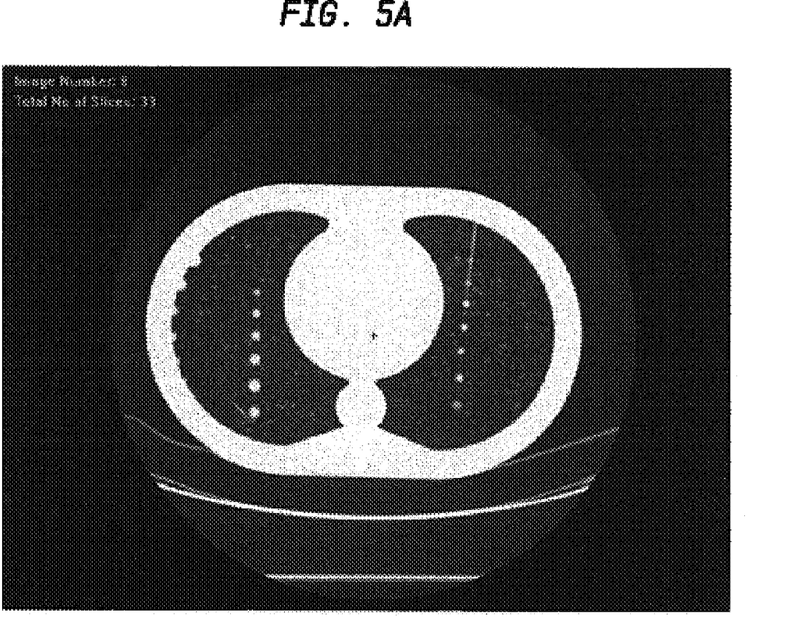
FIG. 5a shows an example input medical image.
Figure 5B:
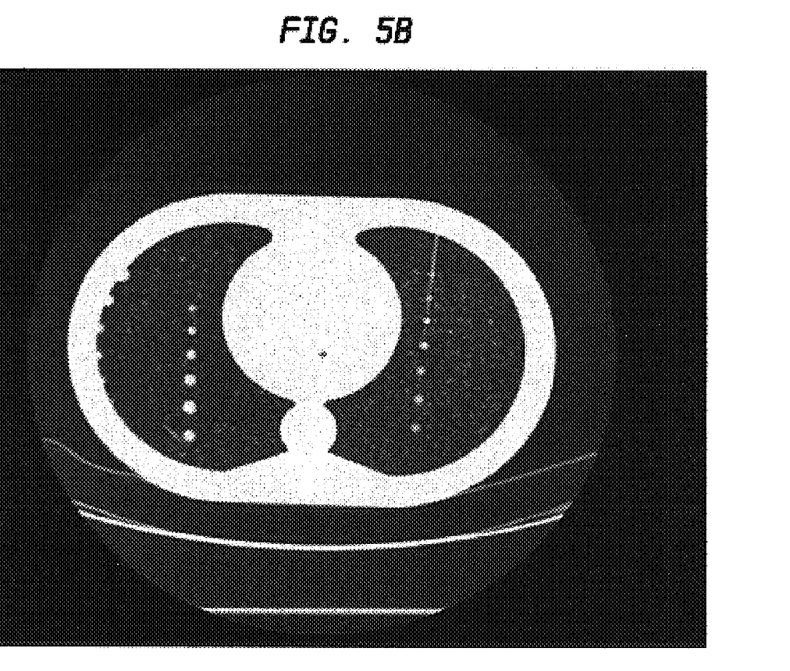
FIG. 5b shows an example result of processing the input medical image with a sphericity enhancement algorithm using optimum parameter values according to an embodiment of the present invention.

One example of such an algorithm 408 is a sphericity enhancement algorithm, which has as input parameters a sphericity threshold, an intensity range and a size range. The sphericity enhancement filter analyzes each volume element (voxel) in a 3D scan image and compares each voxel with surrounding voxels of similar intensity to derive a 3-dimensional (3D) curvature of a surface of equal intensity. Surfaces having a sphericity exceeding the sphericity parameter are identified as belonging to spherical objects. Voxels contained within those surfaces are grouped together as parts of the same object. Once all such objects have been identified, those having a maximum intensity within the intensity range and a size within the size range are indicated in the analysis result 410. The sphericity enhancement algorithm is used to identify nodules in images of the lung, such as lung CT images. FIG. 5*a* shows an example single slice CT image of a lung phantom. FIG. 5*b* shows the image of FIG. 5*a* after processing by the sphericity enhancement algorithm using the optimum parameters.

Other examples of algorithms and their input parameters include an edge enhancement filter having edge enhancement parameters, for detecting abnormalities in the lung parenchyma, and a polyp filter having flatness parameters, for detecting objects having a spherical element and a flatness between maximum and minimum flatness values, for detecting polyps in the colon.

The algorithm 408 may be selected from a plurality of different available algorithms, based for example on some or all of the image metadata 402. The optimum parameter values 406 may then be derived for the selected algorithm 408.

VI. Optimum Parameter Derivation

Referring to step 306, methods of deriving the relationship between metadata values and optimum parameter values will now be described. The relationship may be derived by theoretical knowledge of the effect of image attributes on the optimum parameters, or empirically. In an empirical method, a large number of training images, having known attributes which vary among the training images, are processed using the algorithm for which the relationship is to be determined. The training images may be images of real patients or of phantoms (i.e., objects simulating structures in the body and having known attributes). The processing may be controlled by one or more experienced users able to select the parameter values for the algorithm manually (for example, using the CAR® software described above). Preferably, the experienced users are experienced radiologists and/or experienced users of the algorithm. The training images may also be inspected visually by experienced radiologists to determine as accurately as possible any abnormalities in the training images. The optimum parameter values for each training image may be determined as the parameter values for which the results of the algorithm most closely match the results of the visual inspection and/or as the optimum parameter values chosen by the experienced users. Each training image may be associated with multiple sets of determined optimum parameter values, depending on the sensitivity/specificity requirements of the user.

Alternatively, the training images may include metadata indicating the results of analysis performed automatically and/or by visual inspection using the training images. The optimum parameter values for each training image may be determined as the parameter values for which the results of the algorithm most closely match the results of the analysis as indicated by the metadata.

The result of the processing is a set of one-to-one relationships between the attribute values of each of the training images and the determined optimum parameter values for the respective training images. The attribute values and optimum parameter values for each training image may be stored as training image data sets. However, the set of relationships should be generalized to one or more general relationships which can be applied to new images and their respective attribute values.

Figure 6:
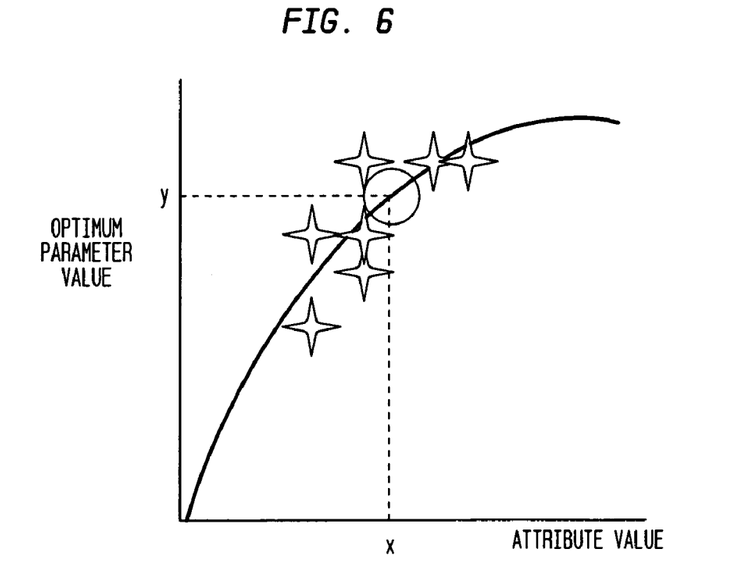
FIG. 6 is a graph illustrating a relationship between attribute values and optimum parameters according to an embodiment of the present invention.

In a simplified example, a single image attribute value may be plotted against a single optimum parameter value, as shown in FIG. 6. The result points from the training images are shown as stars, and a curve is then fitted to these points. The curve represents the generalized relationship in this example. To analyze a new image in an embodiment of the invention, a new attribute value x of the image is input, and the corresponding optimum parameter value y is derived from the curve. Hence, the curve represents the relationship between the attribute value and the optimum parameter value. The general relationship may involve more than one attribute, more than one parameter value, and/or a more complex relationship between them. The general relationship may comprise one or more functions, one or more rules, a neural net and/or fuzzy logic, to provide some examples.

Figure 7:
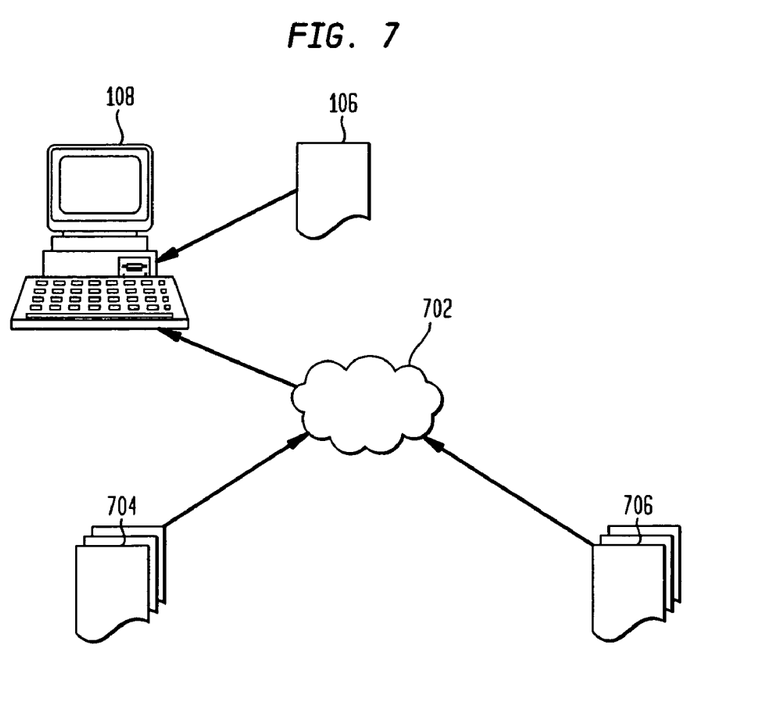
FIG. 7 is a system in which multiple training images are accessed over a network.

As described above, the optimum parameter values may be derived from one or more training images. The training images are digital medical images which may be stored locally or accessed over a local or wide-area network. For example, as shown in FIG. 7, the training images may be accessed using a picture archiving and communication system (PACS) network 702 to access multiple distributed sources of medical images 704, 706.

The training images may be selected from a large number of available digital medical images by searching for images using one or more search criteria and/or by selecting a desired set of images as the training images for optimum parameter derivation. The selected training images may be processed automatically to derive optimum parameters based on the selected training images.

To derive the generalized relationship, only the stored datasets, including the metadata and the optimum parameter values for the training images, need to be accessed. It is not necessary to access the training images themselves.

By selecting the training images used to derive the optimum parameters, the user may customize the optimum parameters for a particular image type represented by the training images. For example, the user may wish to optimize the parameters for a new CT scanner 102. By selecting training images produced by other CT scanners of the same type, the user may configure the parameter values for the new CT scanner, without having to derive these by trial and error.

The user may weight the training images used to derive the optimum parameters, so as to give greater weight to those images which are more relevant to the application desired by the user. For example, the user may derive the optimum parameters for a specific patient using, as training images, previous scan images for that patient and scan images for other patients produced by the same scanner 102. In this example, the user may select a higher weight for the previous scan images of the same patient than for scan images of other patients.

The parameters used by the algorithm may be optimized according to specific criteria, which can be selected by a user. For example, the user can specify that the parameters be optimized for greater sensitivity, or for greater specificity (e.g., so as to avoid false positives). Where the test images have multiple sets of optimum parameter values depending on sensitivity/specificity requirements, the general relationship may be derived from the set corresponding to the user's requirements.

Alternatively, the user may specify other criteria, such as the user's level of experience. Experienced radiologists may be able to tolerate a greater sensitivity setting, because they are more easily able to reject false positives. Less experienced radiologists may prefer a lower sensitivity. Thus, the user need not specify explicitly the required sensitivity. Instead, the user may specify the user's level of experience, from which a required sensitivity level may be derived.

The optimum parameters used by the algorithm may be adjusted adaptively according to the results of the algorithm based on past scans. In other words, scan images processed by the algorithm may be used automatically as training images to optimize the parameters for processing subsequent scans using the algorithm.

VII. Optimum Parameter Defaults

In the embodiments described above, the optimum parameter values 406 are used as input to the algorithm 408. Advantageously, this reduces the need for the user to set parameter values manually. In an alternative embodiment, the derived optimum parameter values 406 are set as default values which may be adjusted by the user.

Figure 8:
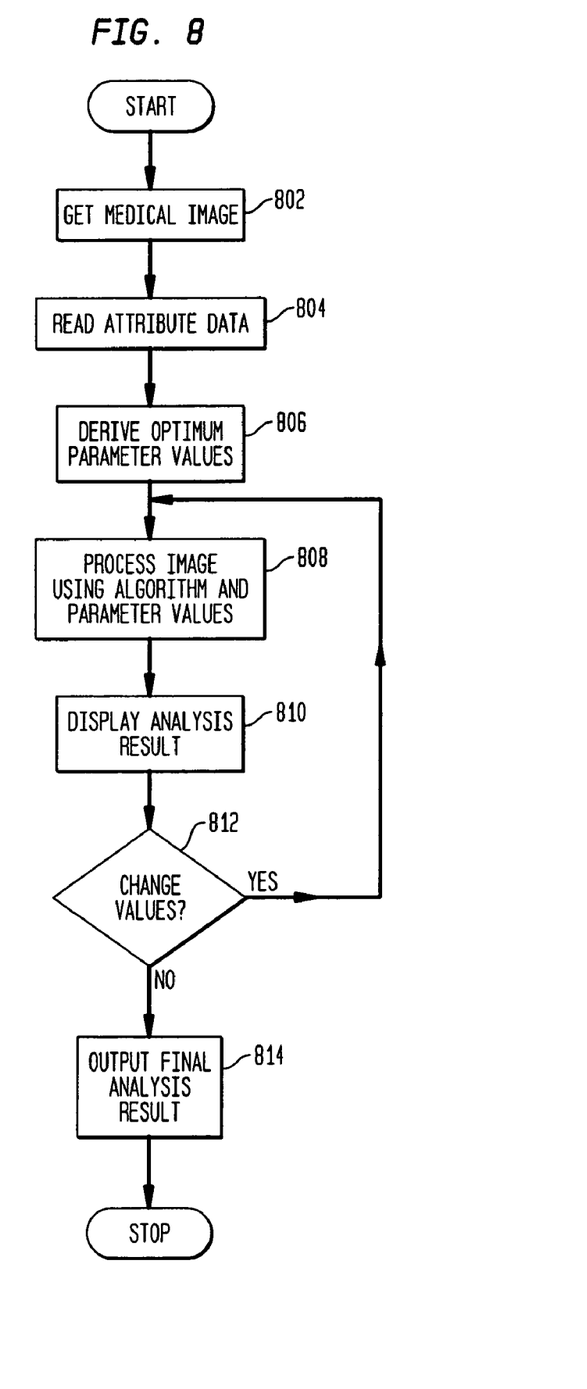
FIG. 8 is a flow chart of the main steps of a method that allows a user to modify optimum parameter values according to an embodiment of the present invention.

FIG. 8 is a flow chart of the main steps of a method that allows a user to modify optimum parameter values according to an embodiment of the present invention. The invention, however, is not limited to the description provided by flowchart 800. Rather, it will be apparent to persons skilled in the relevant art(s) from the teachings provided herein that other functional flows are within the scope and spirit of the present invention.

Referring now to FIG. 8, steps 802 to 808 correspond to steps 302 to 308 of flowchart 300 in FIG. 3. In FIG. 8, the result provided by processing the image using the derived optimum parameter values is displayed at step 810. A user interface includes means to allow the user to modify some or all of the parameter values. If the user does not change the parameter values, as determined at step 812, then the final analysis result is output at step 814. However, if the user modifies the parameter values, as determined at step 812, the image is re-processed at step 808 using the modified parameter values, and the analysis results are re-displayed at step 810, until the user confirms that the parameter values are not to be changed (i.e., the current parameter values are to be accepted) at step 812. The final analysis result is output at step 814 using the accepted parameter values.

Figure 9:
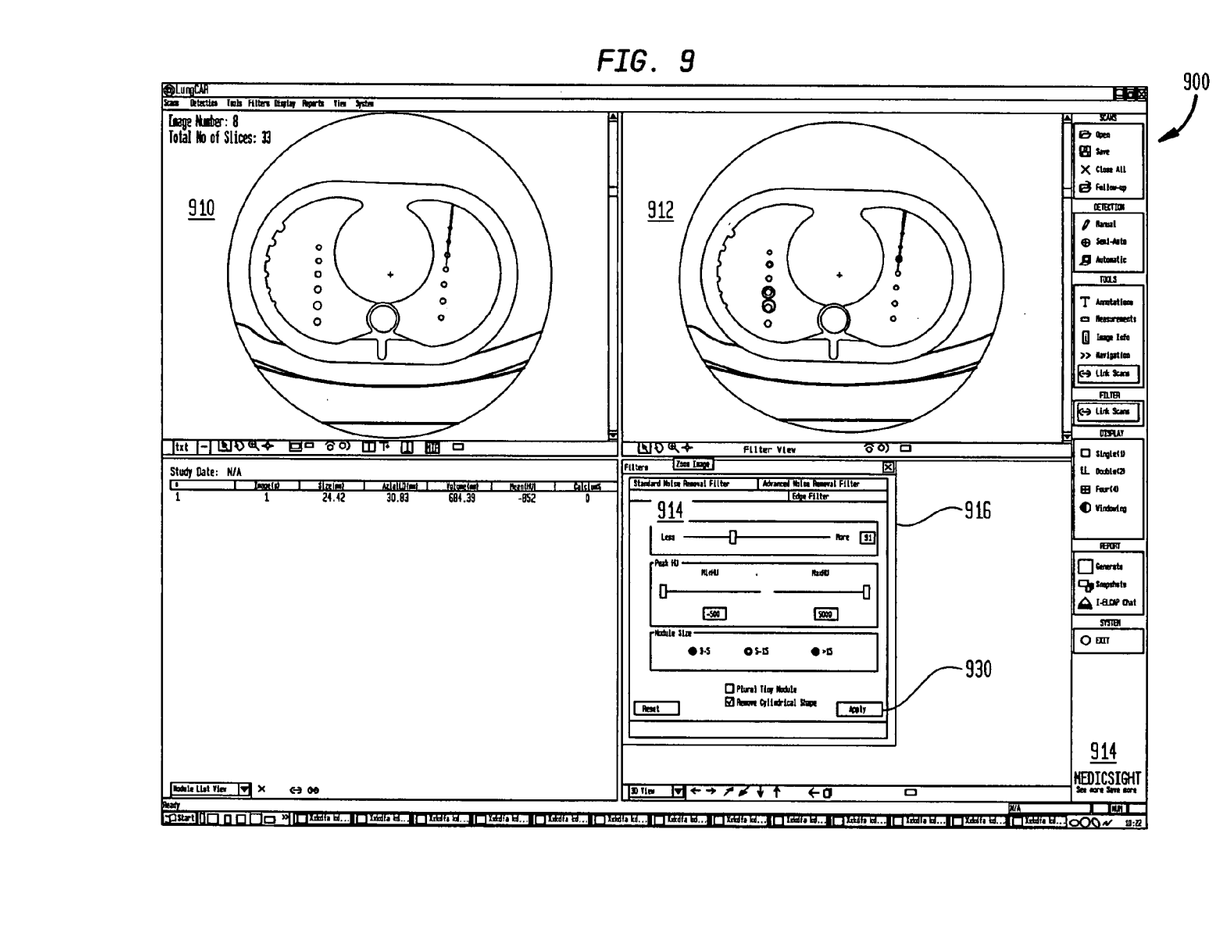
FIG. 9 is a screenshot of a user interface for modifying the parameter values according to an embodiment of the present invention.

FIG. 9 shows a screenshot 900 of a user interface for modifying the parameter values as described above with respect to step 812 of flowchart 800. The user interface is shown in a window comprising an original image pane 910 and an enhanced image pane 912. The original image pane 910 displays a two-dimensional slice of a scan of a lung phantom (i.e., a model approximating the lung and containing objects with known properties, used for testing and calibration). The enhanced image pane 912 displays a version of the original image processed by the algorithm 408 so as to highlight features of the original image.

The current parameter values are displayed by a parameter window 916, which allows the user to modify the parameter values. The user may click a button 930 in the parameter window 916 to apply the modified parameter values to update the enhanced image.

In an alternative user interface, a single scan image is displayed in the user interface window. The single scan image can be switched between the original image and an enhanced image by the user, for example by toggling a button in the filter window. Image display parameters are kept unchanged when switching between the original image and the enhanced image, so that the user can easily compare the enhancement and the original image.

VIII. Conclusion

Example embodiments of the methods, systems, and components of the present invention have been described herein. As noted elsewhere, these example embodiments have been described for illustrative purposes only, and are not limiting. Other embodiments are possible and are covered by the invention. Such other embodiments will be apparent to persons skilled in the relevant art(s) based on the teachings contained herein. Thus, the breadth and scope of the present invention should not be limited by any of the above described exemplary embodiments, but should be defined only in accordance with the following claims and their equivalents.

What is claimed is:

1. A method of analyzing a digital medical image using a computer-implemented algorithm having one or more variable input parameters, comprising:
  a. receiving the digital medical image and metadata associated with the digital medical image;
  b. setting one or more parameter values corresponding to one or more of the variable input parameters based on the metadata; and
  c. processing the digital medical image using the algorithm and the one or more parameter values set in step b.

2. The method of claim 1, wherein receiving the digital medical image and the metadata includes receiving metadata that is indicative of an attribute of a patient upon whom the image is based.

3. The method of claim 2, wherein receiving the digital medical image and the metadata includes receiving metadata that is indicative of the attribute that includes at least one of a clinical indication, historical clinical information, and statistical information.

4. The method of claim 1, wherein receiving the digital medical image and the metadata includes receiving metadata that is indicative of an attribute of an imaging device used to obtain the image.

5. The method of claim 4, wherein receiving the digital medical image and the metadata includes receiving metadata that is indicative of the attribute that at least one of a type of the imaging device and a setting of the imaging device.

6. The method of claim 1, wherein setting the one or more parameter values includes selecting one or more parameter values from a plurality of parameter value sets.

7. The method of claim 1, wherein setting the one or more parameter values includes deriving the one or more parameter values as a predetermined function of the metadata.

8. The method of claim 1, wherein setting the one or more parameter values includes deriving the one or more parameter values from the metadata using at least one of a linear filter, a nonlinear filter, fuzzy logic, and a neural network.

9. The method of claim 1, wherein setting the one or more parameter values includes modifying the one or more parameter values in response to receiving user input to provide modified one or more parameter values, and wherein processing the digital medical image is performed using the algorithm and the modified one or more parameter values.

10. The method of claim 9, further comprising:
displaying a result of the step of processing the digital medical image and the modified one or more parameter values.

11. The method of claim 10, wherein displaying the result includes displaying the result that includes a modified version of the digital medical image to enable a visual comparison of the digital medical image and the modified version.

12. The method of claim 11, wherein displaying the result includes displaying the digital medical image and the modified image simultaneously.

13. The method of claim 11, wherein displaying the result includes displaying the digital medical image and the modified image alternately.

14. A method of deriving a set of one or more optimum parameter values to be provided to a computer-implemented algorithm to analyze a candidate digital medical image having associated metadata, comprising:
   a. accessing a plurality of training digital medical image data sets each including metadata associated with a corresponding digital medical image;
   b. deriving a relationship between values of the metadata and optimum parameter values of corresponding training digital medical image data sets; and
   c. deriving, based on the relationship and on metadata of the candidate digital medical image, the set of optimum parameter values for the candidate digital medical image.

15. The method of claim 14, wherein accessing the plurality of training digital medical image data sets includes accessing training digital medical image data sets, each set including metadata that is indicative of an attribute of a patient upon whom the image is based.

16. The method of claim 14, wherein accessing the plurality of training digital medical image data sets includes accessing training digital medical image data sets, each set including metadata that is indicative of an attribute of an imaging device used to obtain the image.

17. The method of claim 14, further comprising:
inputting the metadata by a user.

18. The method of claim 14, wherein deriving the relationship includes deriving a relationship corresponding to a selection from a plurality of parameter value sets based on the values of the metadata.

19. The method of claim 14, wherein deriving the relationship includes deriving a relationship that includes a predetermined function based on the metadata.

20. The method of claim 14, wherein deriving the relationship includes deriving a relationship that is based on a neural network.

21. The method of claim 14, wherein deriving the relationship includes deriving a relationship that includes a fuzzy logic relationship.

22. The method of claim 14, wherein accessing the plurality of training digital medical image data sets includes locally accessing training digital medical image data sets.

23. The method of claim 14, wherein accessing the plurality of training digital medical image data sets includes accessing training digital medical image data sets over a network.

24. The method of claim 23, wherein accessing the plurality of training digital medical image data sets includes accessing training digital medical image data sets over a network that includes at least one of a local area network, a wide area network, and a PACS network.

25. The method of claim 14, wherein accessing the plurality of training digital medical image data sets includes selecting training digital medical image data sets for access using a predetermined criterion.

26. The method of claim 14, wherein deriving the relationship includes weighting the training image data sets.

27. The method of claim 14, wherein deriving the relationship includes receiving as input a user preference for optimization of the parameter values.

28. An article comprising a computer readable medium for storing instructions to enable a processor-based system to perform operations to analyze a digital medical image using a computer-implemented algorithm having one or more variable input parameters, the operations comprising:
receiving the digital medical image and metadata associated with the digital medical image;
setting one or more parameter values of corresponding one or more of the variable input parameters based on the metadata; and
processing the digital medical image using the algorithm and the one or more parameter values.

29. An article comprising a computer readable medium for storing instructions to enable a processor-based system to perform operations to derive a set of one or more optimum parameter values to be provided to a computer-implemented algorithm to analyze a candidate digital medical image having associated metadata, the operations comprising:
accessing a plurality of training digital medical image data sets each including metadata associated with a corresponding digital medical image;
deriving a relationship between values of the metadata and optimum parameter values of corresponding training digital medical image data sets; and
deriving, based on the relationship and on metadata of the candidate digital medical image, the set of optimum parameter values for the candidate digital medical image.

* * * * *

UNITED STATES PATENT AND TRADEMARK OFFICE
CERTIFICATE OF CORRECTION

| | | |
|---|---|---|
| PATENT NO. | : 7,133,546 B2 | Page 1 of 1 |
| APPLICATION NO. | : 11/138956 | |
| DATED | : November 7, 2006 | |
| INVENTOR(S) | : Dehmeshki et al. | |

It is certified that error appears in the above-identified patent and that said Letters Patent is hereby corrected as shown below:

In column 2, line 29, "greater than 300 RU" should be replaced with --greater than 300 HU--.

In column 12, line 60, "indicative of the attribute that at least one of a type" should be replaced with --indicative of the attribute that is at least one of a type--.

Signed and Sealed this

Eighth Day of May, 2007

JON W. DUDAS
*Director of the United States Patent and Trademark Office*